United States Patent
Knust et al.

(10) Patent No.: US 7,514,426 B2
(45) Date of Patent: *Apr. 7, 2009

(54) SUBSTITUTED IMIDAZOL[1,5-A][1,2,4]TRIAZOLO[1,5-D][1,4]BENZODIAZEPINE DERIVATIVES

(75) Inventors: Henner Knust, Rheinfelden (DE); Andrew William Thomas, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 534 days.

This patent is subject to a terminal disclaimer.

(21) Appl. No.: 11/252,025

(22) Filed: Oct. 17, 2005

(65) Prior Publication Data

US 2006/0084642 A1    Apr. 20, 2006

(30) Foreign Application Priority Data

Oct. 20, 2004    (EP)    ................... 04105169

(51) Int. Cl.
*A61P 25/28*    (2006.01)
*A61K 31/55*    (2006.01)
*C07D 243/00*    (2006.01)

(52) U.S. Cl. ..................... 514/219; 540/555
(58) Field of Classification Search .................. 514/219; 540/555
See application file for complete search history.

(56) References Cited

U.S. PATENT DOCUMENTS

| 4,316,839 A | 2/1982  | Gerecke et al. |
| 4,772,599 A | 9/1988  | Wätjen |
| 4,775,671 A | 10/1988 | Hunkeler et al. |
| 4,897,392 A | 1/1990  | Tegeler et al. |
| 5,387,585 A | 2/1995  | Borer et al. |

FOREIGN PATENT DOCUMENTS

| EP | 0 027 214  | 4/1981 |
| EP | 0 150 040  | 7/1985 |
| EP | 0 519 307  | 12/1992 |
| EP | 1 337 535 A | 8/2003 |
| WO | WO 02/40487 | 5/2002 |

OTHER PUBLICATIONS

McNamara, et al., Psychobiology (1993), vol. 21(2) pp. 101-108.
Gerecke, et al., Heterocycles (1994), vol. 39, No. 2, pp. 693-721.
Breuer, Tetrahedron Letters (1976) No. 23, pp. 1935-1938.
Möhler et al., Nature (1981) vol. 294 pp. 763-765.
Möhler et al., Journal of Neurochemistry (1981), vol. 37(3), pp. 714-722.
Chemical Abstract 204054p, vol. 90, 1979 p. 624.
Chemical Abstract 37799s, vol. 108, 1988 p. 635.
Drug Evaluations, 6th Ed. (1986), American Medical Association, pp. 160-162.
Thompson et al., The New England Journal of Medicine (1990), vol. 323(7) pp. 445-448.
Rennie, Scientific American (1992) pp. 20 & 26.
Berkow et al., The Merck Manual of Diagnosis & Therapy, 15th Ed. (1987) pp. 839-840.
Wyngaarden, et al., Cecil Textbook of Medicine, 19th Ed. (1992), pp. 2075-2079.
Wang, Q., et al, CNS Drug Reviews (1999), vol. 5, No. 2, pp. 125-144.
J. Grayson Richards and James R. Martin, Brain Research Bulletin, (1998), vol. 45, No. 4, pp. 381-387.

*Primary Examiner*—Brenda L Coleman
(74) *Attorney, Agent, or Firm*—George W. Johnston; Patricia S. Rocha-Tramaloni; Kimberly J. Prior

(57) ABSTRACT

The present invention is concerned with substituted imidazo[1,5-a][1,2,4]triazolo[1,5-d][1,4]benzodiazepine derivatives of formula I

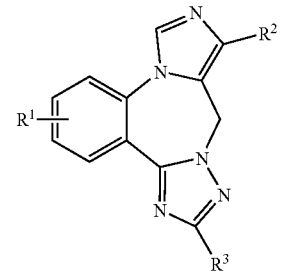

wherein
$R^1$ is hydrogen, halogen, lower alkyl, lower alkynyl, cycloalkyl, heterocycloalkyl, benzyl, cyano, lower alkoxy, $OCF_3$, —NHR, —NHC(O)R or —$NHSO_2R$;
$R^2$ is lower alkyl substituted by halogen;
$R^3$ is hydrogen, methyl or aryl;
R is lower alkyl, cycloalkyl or aryl;
and pharmaceutically acceptable acid addition salts thereof.

15 Claims, No Drawings

SUBSTITUTED IMIDAZOL[1,5-A][1,2,4]TRIAZOLO[1,5-D][1,4] BENZODIAZEPINE DERIVATIVES

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 in channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred

SUMMARY OF THE INVENTION

The present invention provides substituted imidazo[1,5-a][1,2,4]triazolo[1,5-d][1,4]benzodiazepine derivatives of formula I

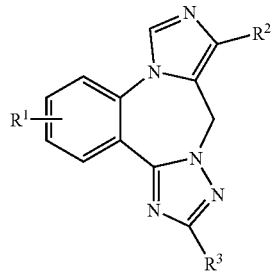

wherein
$R^1$ is hydrogen, halogen, lower alkyl, lower alkynyl, cycloalkyl, heterocycoalkyl, benzyl, cyano, lower alkoxy, $OCF_3$, —NHR, —NHC(O)R or —$NHSO_2R$;
$R^2$ is lower alkyl substituted by halogen;
$R^3$ is hydrogen, methyl or aryl;
R is lower alkyl, cycloalkyl or aryl;

and pharmaceutically acceptable acid addition salts thereof.

The present invention also provides pharmaceutical compositions that comprise compounds of the invention and a pharmaceutical carrier as well as methods for preparing such compositions.

This class of compounds has high affinity and selectivity for GABA A α5 receptor binding sites and might be useful as a cognitive enhancer or for the treatment of cognitive disorders, anxiety, schizophrenia or Alzheimer's disease. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain alkyl group containing from 1-7, preferably from 1-4 carbon atoms, for example, methyl, ethyl, propyl, isopropyl, n-butyl, i-butyl, t-butyl and the like.

The term "halogen" denotes chlorine, iodine, fluorine and bromine.

As used herein, the term "lower alkyl substituted by halogen" denotes a straight- or branched-chain alkyl group containing from 1-7, preferably from 1-4 carbon atoms, for example, methyl, ethyl, propyl, isopropyl, n-butyl, i-butyl, t-butyl and the like, wherein at least one hydrogen atom is replaced by a halogen atom. Examples of preferred groups are $CF_3$, $CHF_2$, $CH_2F$, $CF_2CH_2CH_3$, $CHFCH_2CH_3$ or $CF_2CH_3$.

The term "lower alkoxy" denotes the residue —O—R, wherein R is a lower alkyl residue as defined herein.

The term "lower alkynyl" denotes a straight- or branched-chain carbon group containing from 2-7, preferably from 2-4 carbon atoms, wherein at least one bond is a triple bond.

The term "aryl" denotes a phenyl, benzyl or naphthyl group, which groups maybe substituted by lower alkyl or lower alkoxy.

The term "cycloalkyl" denotes a cyclic alkyl ring, having from 3 to 7 carbon ring atoms, for example, cyclopropyl, cyclopentyl or cyclohexyl.

The term "heterocycloalkyl" denotes a cyclic alkyl ring, having from 3 to 7 carbon ring atoms, wherein at least one carbon atom is replaced by a heteroatom, selected from the group consisting of O, N or S, for example morpholinyl, piperazinyl or piperidinyl.

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Exemplary preferred are compounds, which have a binding activity (Ki) of lower than 30 nM, are selective for GABA A α5 subunits, and are relatively free of activity at GABA A α1, α2 and α3 receptor binding sites.

The present invention provides substituted imidazo[1,5-a][1,2,4]triazolo[1,5-d][1,4]benzodiazepine derivatives of formula I

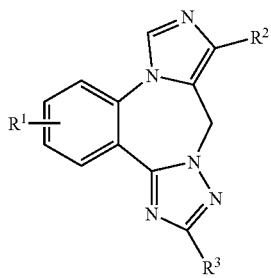

wherein
R$^1$ is hydrogen, halogen, lower alkyl, lower alkynyl, cycloalkyl, heterocycloalkyl, benzyl, cyano, lower alkoxy, OCF$_3$, —NHR, —NHC(O)R or —NHSO$_2$R;
R$^2$ is lower alkyl substituted by halogen;
R$^3$ is hydrogen, methyl or aryl;
R is lower alkyl, cycloalkyl or aryl;

and pharmaceutically acceptable acid addition salts thereof.

In one embodiment, compounds of formula I are those in which R$^2$ is CH$_2$F, for example the following compounds:
3-chloro-10-fluoromethyl-9H-imidazo[1,5-a][1,2,4]triazolo[1,5-d][1,4]benzodiazepine,
3-fluoro-10-fluoromethyl-9H-imidazo[1,5-a][1,2,4]triazolo[1,5-d][1,4]benzodiazepine,
3-bromo-10-fluoromethyl-9H-imidazo[1,5-a][1,2,4]triazolo[1,5-d][1,4]benzodiazepine,
3-cyclopropyl-10-fluoromethyl-9H-imidazo[1,5-a][1,2,4]triazolo[1,5-d][1,4]benzodiazepine and
3-chloro-10-fluoromethyl-6-methyl-9H-imidazo[1,5-a][1,2,4]triazolo[1,5-d][1,4]benzodiazepine.

In another embodiment, the invention provides are compounds, wherein R$^2$ is CHF$_2$, for example the following compounds:
3-chloro-10-difluoromethyl-9H-imidazo[1,5-a][1,2,4]triazolo[1,5-d][1,4]benzodiazepine,
3-fluoro-10-difluoromethyl-9H-imidazo[1,5-a][1,2,4]triazolo[1,5-d][1,4]benzodiazepine,
3-bromo-10-difluoromethyl-9H-imidazo[1,5-a][1,2,4]triazolo[1,5-d][1,4]benzodiazepine,
3-cyclopropyl-10-difluoromethyl-9H-imidazo[1,5-a][1,2,4]triazolo[1,5-d][1,4]benzodiazepine,
10-difluoromethyl-3-ethyl-9H-imidazo[1,5-a][1,2,4]triazolo[1,5-d][1,4]benzodiazepine,
3-benzyl-10-difluoromethyl-9H-imidazo[1,5-a][1,2,4]triazolo[1,5-d][1,4]benzodiazepine,
10-difluoromethyl-3-ethynyl-9H-imidazo[1,5-a][1,2,4]triazolo[1,5-d][1,4]benzodiazepine,
3-cyano-10-difluoromethyl-9H-imidazo[1,5-a][1,2,4]triazolo[1,5-d][1,4]benzodiazepine and
10-difluoromethyl-9H-imidazo[1,5-a][1,2,4]triazolo[1,5-d][1,4]benzodiazepine.

In yet another embodiment, compounds of formula I are those in which R$^2$ is CF$_3$, for example the following compound:
3-fluoro-10-trifluoromethyl-9H-imidazo[1,5-a][1,2,4]triazolo[1,5-d][1,4]benzodiazepine.

In a further embodiment, the invention provides compounds wherein R$^2$ is CF$_2$CH$_3$ or CF$_2$CH$_2$CH$_3$, for example the following compounds:
10-(1,1-difluoro-ethyl)-3-fluoro-9H-imidazo[1,5-a][1,2,4]triazolo[1,5-d][1,4]benzodiazepine,
10-(1,1-difluoro-propyl)-3-fluoro-9H-imidazo[1,5-a][1,2,4]triazolo[1,5-d][1,4]benzodiazepine and
3-bromo-10-(1,1-difluoro-propyl)-9H-imidazo[1,5-a][1,2,4]triazolo[1,5-d][1,4]benzodiazepine.

Furthermore, in one embodiment of the present invention are compounds of formula I-A

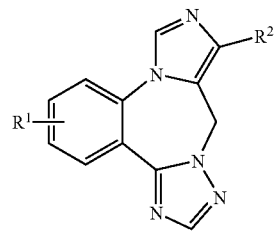

wherein
R$^1$ is hydrogen, halogen, lower alkyl, lower alkynyl, cycloalkyl, benzyl, cyano, lower alkoxy, OCF$_3$, —NHR, —NHC(O)R or —NHSO$_2$R;
R$^2$ is lower alkyl substituted by halogen;
R is lower alkyl, cycloalkyl or aryl;

and pharmaceutically acceptable acid addition salts thereof.

Compounds of formula I and their pharmaceutically acceptable salts can be prepared by methods known in the art, for example, by the processes described below, which processes comprise a) reacting a compound of formula

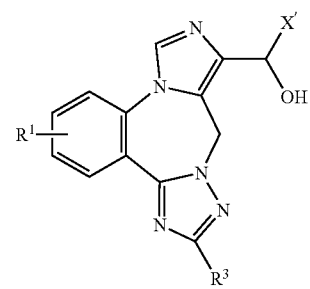

X' = H, lower alkyl with a suitable halogen-transfer-reagent, for example with [bis(2-methoxyethyl)amino]sulfur trifluoride, to produce a compound of formula

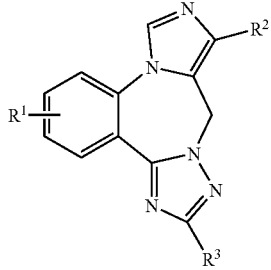

wherein R² is lower alkyl substituted by halogen, and, if desired, converting the compound of formula I into a pharmaceutically acceptable salt thereof, or b) reacting a compound of formula

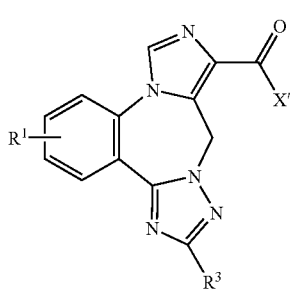

X' = H, lower alkyl with a suitable halogen-transfer-reagent, for example with [bis(2-methoxyethyl)amino]sulfur trifluoride, to produce a compound of formula

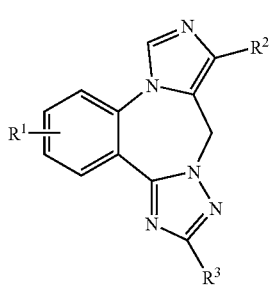

and, if desired, converting the compound of formula I into a pharmaceutically acceptable salt thereof, or c) reacting a compound of formula

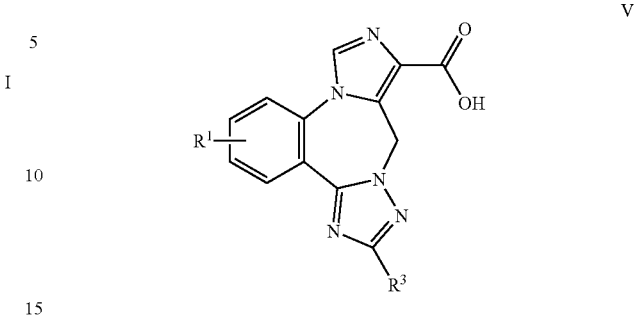

with sulfur tetrafluoride in the presence of a hydrogen halogenide to produce a compound of formula

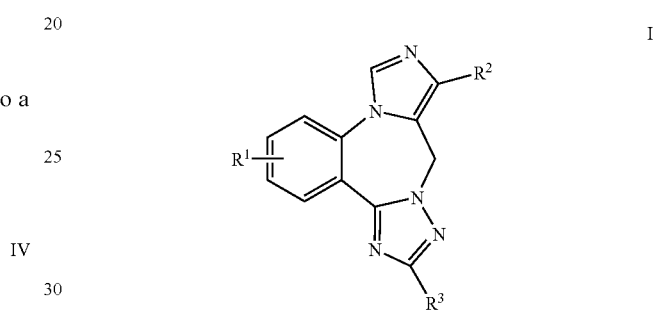

and, if desired, converting the compound of formula I into a pharmaceutically acceptable salt thereof.

In accordance with the present invention, compounds of the formula I can be prepared following process variant a): A compound of formula III is treated with an halogen-transfer-reagent, for example an amino sulfur trifluoride like [bis(2-methoxyethyl)amino]sulfur trifluoride or the like, in a suitable solvent, for example dichloromethane or the like, or even without a solvent at an appropriate temperature.

Furthermore, compounds of formula I may be prepared in accordance with process variant b): A compound of formula IV is treated with an halogen-transfer-reagent, for example an amino sulfur trifluoride like [bis(2-methoxyethyl)amino]sulfur trifluoride or the like, in a suitable solvent, for example dichloromethane or the like, or even without a solvent at an appropriate temperature.

In accordance with process variant c) a compound of formula V is converted by reaction with sulfur tetrafluoride in the presence of hydrogen halogenide, for example hydrogen fluoride, to produce a compound of formula I.

The following schemes (scheme 1-4) describe the processes for preparation of compounds of formula I in more detail. The starting materials are known compounds or may be prepared according to methods known in the art.

Scheme 1

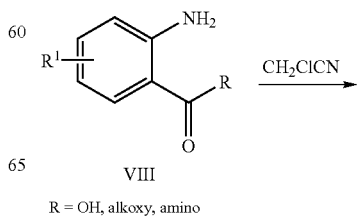

R = OH, alkoxy, amino

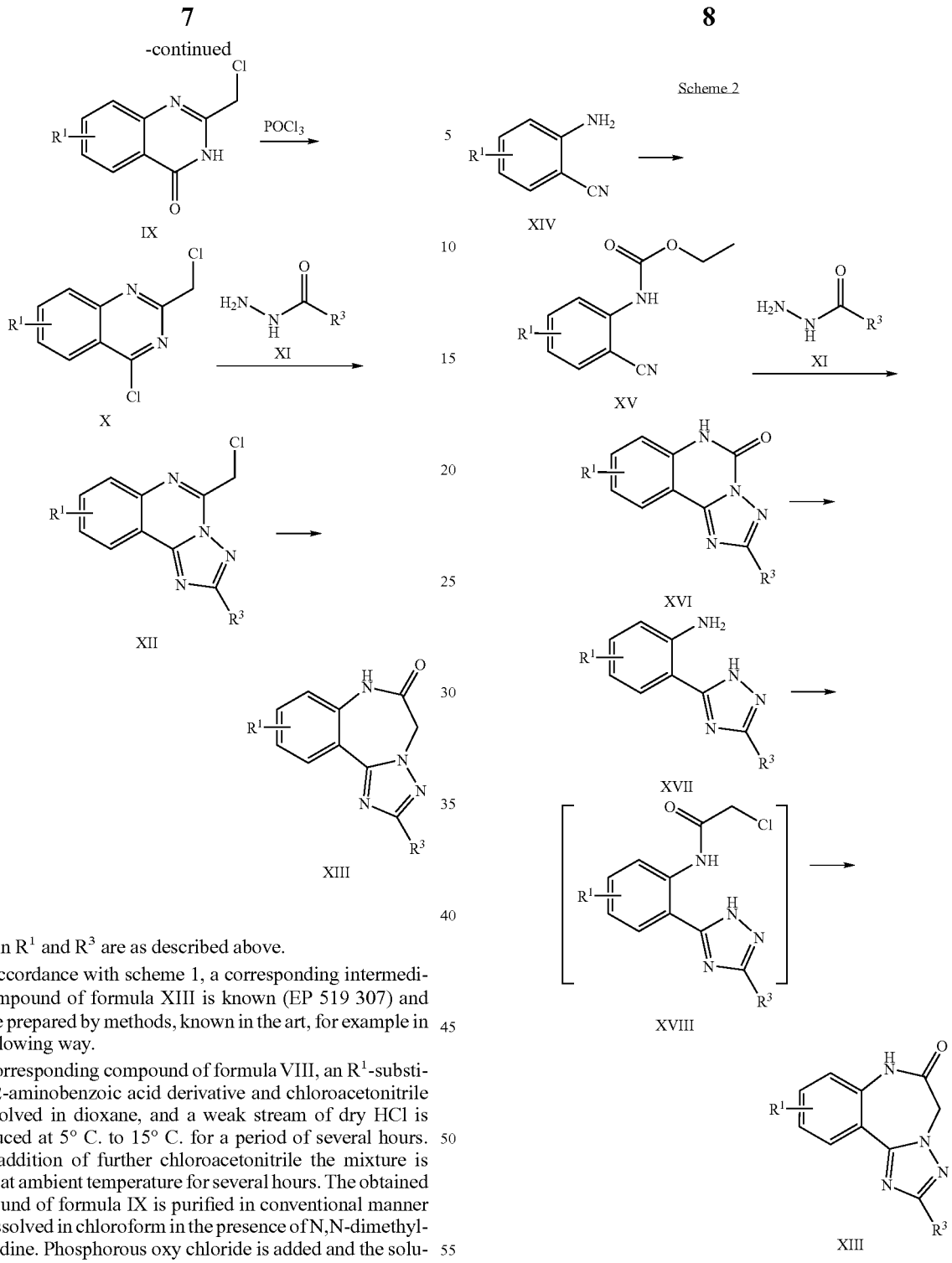

wherein $R^1$ and $R^3$ are as described above.

In accordance with scheme 1, a corresponding intermediate compound of formula XIII is known (EP 519 307) and may be prepared by methods, known in the art, for example in the following way.

A corresponding compound of formula VIII, an $R^1$-substituted 2-aminobenzoic acid derivative and chloroacetonitrile is dissolved in dioxane, and a weak stream of dry HCl is introduced at 5° C. to 15° C. for a period of several hours. After addition of further chloroacetonitrile the mixture is stirred at ambient temperature for several hours. The obtained compound of formula IX is purified in conventional manner and dissolved in chloroform in the presence of N,N-dimethyl-p-toluidine. Phosphorous oxy chloride is added and the solution heated. The obtained compound of formula X is purified by known methods and heated with a compound of formula XI, an acylhydrazide, in toluene for several hours affording a compound of formula XII, for example the compound 5-chloromethyl-9-fluoro-1,2,4-triazolo[4,3-c]quinazoline. Finally, a compound of XIII is obtained by dissolving a compound of formula XII in dioxane followed by treatment with aqueous sodium hydroxide in such manner that the reaction temperature is between 10° C. to 15° C. Conventional workup and purification affords a corresponding intermediate of formula XIII, for example 10-fluoro-5H-[1,2,4]triazolo[1,5-d][1,4]benzodiazepin-6(7H)-one.

wherein $R^1$ and $R^3$ are as described above.

In accordance with scheme 2, a corresponding intermediate compound of formula XIII may be prepared alternatively in the following way:

A corresponding compound of formula XIV, an $R^1$-substituted 2-aminobenzonitrile, is heated with ethyl chloroformate to obtain a carbamic acid ester of formula XV, which is treated with a compound of formula XI, an acylhydrazide, in 1-methyl-2-pyrrolidone at 160° C. under removal of ethanol. Conventional workup provides a urea of formula XVI, which is heated with aqueous sodium hydroxide in ethylene glycol to obtain a compound of formula XVII. Treatment of a compound of formula XVII with chloroacetyl chloride in acetic acid provides an amide of formula XVIII, which is treated with aqueous sodium hydroxide in dioxane at ambient temperature to obtain the intermediate of formula XIII. Alternatively, a compound of formula XVII can be directly transformed to a compound of formula XIII by dissolving a compound of formula XVII in dioxane and pyridine and adding dropwise chloroacetyl chloride at a temperature between 10° C. to 15° C. After stirring for a short period of time aqueous sodium hydroxide is added, and the reaction mixture stirred for several hours at ambient temperature to obtain the compound of formula XIII.

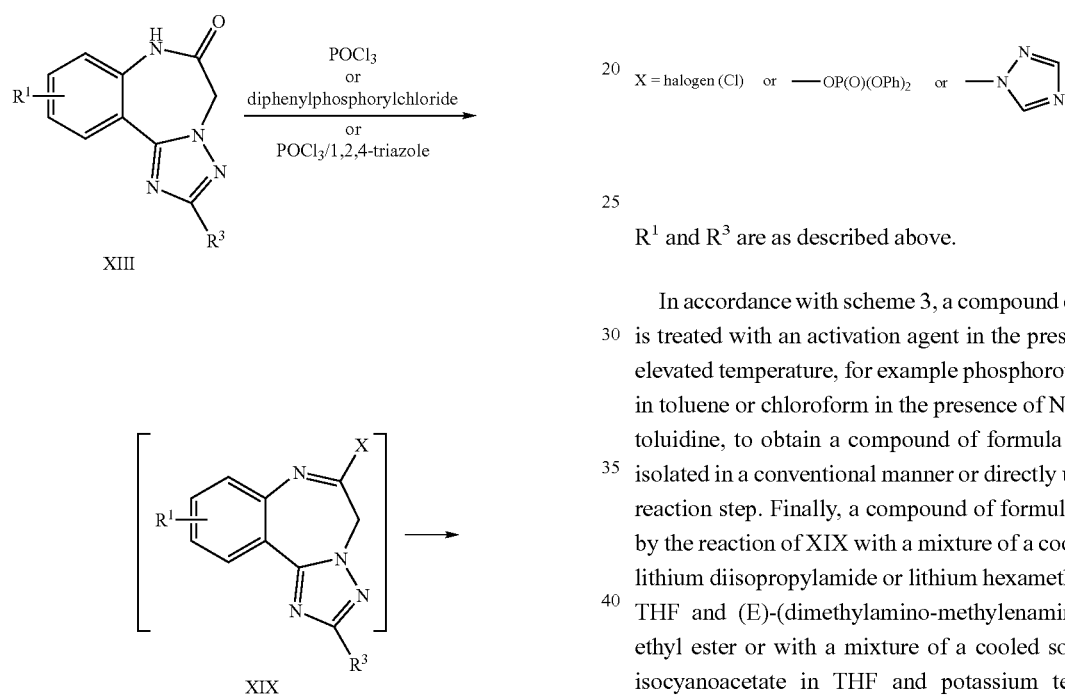

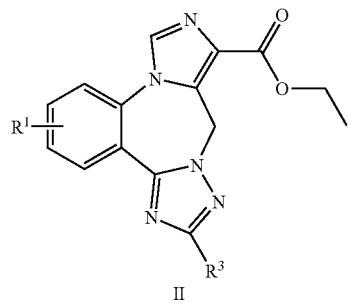

$X$ = halogen (Cl) or —OP(O)(OPh)$_2$ or [triazolyl]

$R^1$ and $R^3$ are as described above.

In accordance with scheme 3, a compound of formula XIII is treated with an activation agent in the presence of base at elevated temperature, for example phosphorous oxy chloride in toluene or chloroform in the presence of N,N-dimethyl-p-toluidine, to obtain a compound of formula XIX, which is isolated in a conventional manner or directly used in the next reaction step. Finally, a compound of formula II is obtained by the reaction of XIX with a mixture of a cooled solution of lithium diisopropylamide or lithium hexamethyldisilazide in THF and (E)-(dimethylamino-methylenamino)-acetic acid ethyl ester or with a mixture of a cooled solution of ethyl isocyanoacetate in THF and potassium tert-butoxide or sodium hydride.

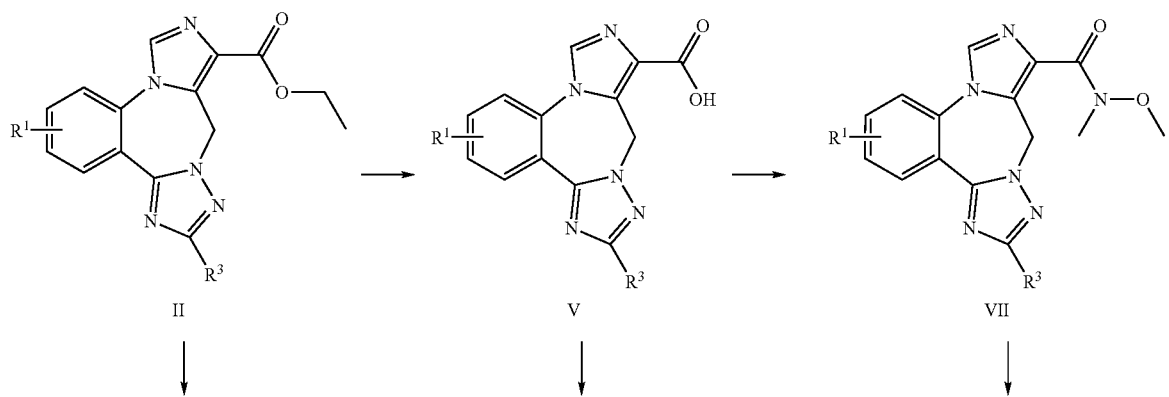

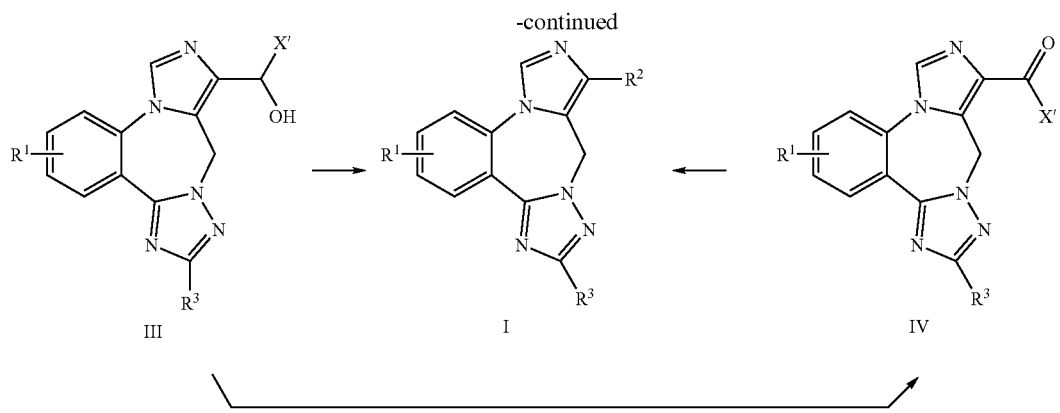

wherein X' is hydrogen or lower alkyl and R¹, R² and R³ are as described above.

According to scheme 4, a compound of formula II is heated with lithiumborohydride in tetrahydrofuran to obtain a compound of formula III which is treated with [bis(2-methoxyethyl)amino]sulfur trifluoride in dichloromethane at ambient temperature affording a compound of formula I. Alternatively) a compound of formula II is hydrolyzed to a carboxylic acid of formula V which is converted by reaction with sulfur tetrafluoride in the presence of hydrogen fluoride to produce a compound of formula I. Reaction of a compound of formula V with an activation reagent, for example 1-(3-dimethylaminopropyl)-3-ethylcarbodiimide hydrochloride, in the presence of N,O-dimethylhydroxylamine hydrochloride and a base, for example N-methylmorpholine, in a solvent mixture of dichloromethane and DMF at ambient temperature affords a compound of formula VII which is reduced using diisobutylaluminium hydride in dichloromethane to obtain an aldehyde of formula IV or transformed into a ketone IV by reaction with an appropriate reagent, for example a Grignard-reagent. This ketone or aldehyde (IV), which is also be obtained by an oxidation of an alcohol of formula III by treatment with manganese(IV) oxide (or Dess Martin periodinane) in dichloromethane at ambient temperature, is treated with [bis(2-methoxyethyl)amino]sulfur trifluoride with or without dichloromethane as solvent at ambient or elevated temperature to obtain a compound of formula I.

As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter.

MEMBRANE PREPARATION AND BINDING ASSAY

The affinity of compounds at GABA A receptor subtypes was measured by competition for [³H]flumazenil (85 Ci/mmol; Roche) binding to HEK293 cells expressing rat (stably transfected) or human (transiently transfected) receptors of composition α1β3γ2, α2β3γ2, α3β3γ2 and α5βγ2.

Cell pellets were suspended in Krebs-tris buffer (4.8 mM KCl, 1.2 mM CaCl₂, 1.2 mM MgCl₂, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 μL (96-well plates) which contained 100 μL of cell membranes, [³H]flumazenil at a concentration of 1 nM for α1, α2, α3 subunits and 0.5 nM for α5 subunits and the test compound in the range of $10^{-10}$-$3\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [³H]flumazenil from α5 subunits of the rat GABA A receptor of 100 nM or less. In a preferred embodiment the compounds of the invention are binding selective for the α5 subunit relative to the α1, α2 and α3 subunit.

The table below shows the activity data for some specific compounds:

| Example No. | Ki[nM] hα1 | Ki[nM] hα2 | Ki[nM] hα3 | Ki[nM] hα5 |
|---|---|---|---|---|
| 1 | 59.1 | 67.0 | 40.0 | 9.4 |
| 2 | 52.9 | 81.3 | 47.9 | 5.6 |
| 3 | 49.9 | 25.4 | 26.2 | 9.1 |
| 4 | 34.4 | 14.4 | 15.6 | 6.8 |
| 5 | 39.0 | 23.9 | 27.7 | 7.0 |
| 6 | 215.0 | 261.2 | 107.5 | 8.7 |
| 7 | 174.3 | 185.4 | 79.6 | 4.6 |
| 8 | 271.8 | 275.6 | 269.7 | 14.7 |
| 9 | 215.6 | 160.5 | 191.9 | 13.3 |
| 10 | 272.2 | 624.1 | 480.4 | 31.7 |
| 11 | 455.1 | 903.6 | 487.6 | 26.4 |
| 12 | 1458 | 416.4 | 512.2 | 16.9 |
| 13 | 246.2 | 246.3 | 105.8 | 16.5 |
| 14 | 162.9 | 98.8 | 73.5 | 26.6 |
| 15 | 15.0 | 11.3 | 8.9 | 3.2 |
| 16 | 28.3 | 13.9 | 10.5 | 1.6 |
| 17 | 1875 | >3160 | >3160 | 271.5 |
| 18 | 787.2 | 764.2 | 649.9 | 37.5 |

-continued

| Example No. | Ki[nM] hα1 | Ki[nM] hα2 | Ki[nM] hα3 | Ki[nM] hα5 |
|---|---|---|---|---|
| 19 | 32.9 | 146.7 | 77.2 | 6.4 |
| 20 | 50.1 | 181.0 | 116.7 | 2.5 |
| 21 | >3160 | >3160 | >3160 | 151.6 |

The present invention also provides pharmaceutical compositions containing one or more compounds of the invention, for example a compound of formula I or their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the present invention are GABA A α5 receptor inhibitors. The invention also provides a method for enhancing cognition or for treating a disorder selected from the group consisting of cognitive disorders, anxiety, schizophrenia and Alzheimer's disease which comprises administering to an individual a therapeutically effective amount of a compound of formula I or a pharmaceutically acceptable salt thereof. In particular, the invention provides a method for treating Alzheimer's disease which comprises administering to an individual a therapeutically effective amount of a compound of formula I or a pharmaceutically acceptable salt thereof.

The compounds and compositions of the present invention can be administered in a conventional manner, for example, orally, rectally, or parenterally. The compounds of the invention can be administered orally, for example, in the form of tablets, coated tablets, dragées, hard and soft gelatine capsules, solutions, emulsions, or suspensions. The compounds of the invention can be administered rectally, for example, in the form of suppositories or parenterally, for example, in the form of injectable solutions.

The dosage at which the compound of the invention is administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof.

EXAMPLE 1

3-Chloro-10-fluoromethyl-9H-imidazo[1,5-a][1,2,4]triazolo[1,5-d][1,4]benzodiazepine a) 3-Chloro-10-hydroxymethyl-9H-imidazo[1,5-a][1,2,4]triazolo[1,5-d][1,4]benzodiazepine To a suspension of ethyl 3-chloro-9H-imidazo[1,5-a][1,2,4]triazolo[1,5-d][1,4]benzodiazepine-10-carboxylate (EP 519 307) (10.0 g, 30.3 mmol) in THF (400 mL) was added lithium borohydride (800 mg, 34.9 mmol) and the reaction mixture was heated to reflux for 7 hrs. After cooling to ambient temperature, it was acidified to pH=2 by adding aq HCl 1N and diluted with water (50 mL). The solvent was evaporated and the residue was taken in aq. $NH_4OH$ (conc., 100 mL). The resulting solid were filtered off, washed with water (3×10 mL) and dried (60° C., vacuo) affording the title compound (4.01 g, 45.8%) as a white solid. MS: m/e=287.9 ($M^+$).

b) 3-Chloro-10-fluoromethyl-9H-imidazo[1,5-a][1,2,4]triazolo[1,5-d][1,4]benzodiazepine To a suspension of 3-chloro-10-hydroxymethyl-9H-imidazo[1,5-a][1,2,4]triazolo[1,5-d][1,4]benzodiazepine (193 mg, 0.67 mmol) in dichloromethane (6 mL) was added at −70° C. bis(2-methoxyethyl)aminosulphur trifluoride (0.08 ml, 0.74 mmol). The reaction mixture was stirred for 18 h while allowing to warm to ambient temperature. Dichloromethane (20 mL) was added and the mixture was washed with aq $Na_2CO_3$, dried over sodium sulfate and concentrated in vacuo. The residue was purified by chromatography ($SiO_2$, ethyl acetate:dichloromethane:methanol=75:20:5) affording the title compound (87 mg, 45%) as a white solid. MS: m/e=289.9 ($M^+$).

EXAMPLE 2

3-Chloro-10-difluoromethyl-9H-imidazo[1,5-a][1,2,4]triazolo[1,5-d][1,4]benzodiazepine a) 3-Chloro-9H-imidazo[1,5-a][1,2,4]triazolo[1,5-d][1,4]benzodiazepine-10-carbaldehyd To a solution of 3-chloro-10-hydroxymethyl-9H-imidazo[1,5-a][1,2,4]triazolo[1,5-d][1,4]benzodiazepine (15.0 g, 52.1 mmol) in dichloromethane (1.5 L) was added manganese(IV) oxide (188 g, 1.94 mol) and the mixture was stirred at ambient temperature for 24 h. It was filtered over dicalite, washed with dichlormethane and concentrated. The residue was dissolved in dichlormethane (700 mL) at 40° C. and ethyl acetate (100 mL) was added. The product started to crystallise. After cooling the dichloromethane was evaporated and the solid filtered. Drying in vacuo afforded the title compound (11.8 g, 79.2%) as a yellow crystalline solid. MS: m/e=286.1 ($M+H^+$).

b) 3-Chloro-10-difluoromethyl-9H-imidazo[1,5-a][1,2,4]triazolo[1,5-d][1,4]benzodiazepine To a suspension of 3-chloro-9H-imidazo[1,5-a][1,2,4]triazolo[1,5-d][1,4]benzodiazepine-10-carbaldehyde (600 mg, 2.10 mmol) in dichloromethane (18 mL) was added, at −70° C. under argon, bis(2-methoxyethyl)aminosulphur trifluoride (0.47 mL, 4.62 mmol). The reaction mixture was stirred for 18 h while allowed to warm to ambient temperature. Again, bis(2-methoxyethyl)-aminosulphur trifluoride (0.2 mL) was added and stirring was continued for another 18 h at 40° C. The mixture was diluted with ethyl acetate and washed with aq $Na_2CO_3$, dried over sodium sulfate and concentrated in vacuo. The residue was purified by chromatography ($SiO_2$, heptane:ethyl acetate:dichloromethane=6:2:2) affording the title compound (403 mg, 62%) as a white solid. MS: m/e=308.2 ($M+H^+$).

EXAMPLE 3

3-Fluoro-10-fluoromethyl-9H-imidazo[1,5-a][1,2,4]triazolo[1,5-d][1,4]benzodiazepine a) 3-Fluoro-10-hydroxymethyl-9H-imidazo[1,5-a][1,2,4]triazolo[1,5-d][1,4]benzodiazepine To a suspension of ethyl 3-fluoro-9H-imidazo[1]5-a][1,2,4]triazolo[1,5-d][1,4]benzodiazepine-10-carboxylate (EP 519 307) (9.24 g, 29.5 mmol) in THF (300 mL) was added lithium borohydride (811 mg, 35.4 mmol) and the reaction mixture was heated to reflux for 8 hrs. After cooling to ambient temperature, it was acidified to pH=2 by adding aq HCl 1N. The solvent was evaporated and the residue was taken in aq. $NH_4OH$ (conc., 100 mL). The resulting solid were filtered off, washed with water (3×10 mL) and dried (60° C., vacuo) affording the title compound (6.53 g, 83%) as a white solid. MS: m/e=272.2 ($M+H^+$).

b) 3-Fluoro-10-fluoromethyl-9H-imidazo[1,5-a][1,2,4]triazolo[1,5-d][1,4]benzodiazepine As described for example 1b, 3-fluoro-10-hydroxymethyl-9H-imidazo[1,5-a][1,2,4]triazolo[1,5-d][1,4]benzodiazepine (522 mg, 1.93 mmol), instead of 3-chloro-10-hydroxymethyl-9H-imidazo[1,5-a][1,2,4]triazolo[1,5-d][1,4]benzodiazepine, was converted to the title compound (279 mg, 53%) which was obtained as a white solid. MS: m/e=274.1 ($M+H^+$).

EXAMPLE 4

3-Fluoro-10-difluoromethyl-9H-imidazo[1,5-a][1,2,4]triazolo[1,5-d][1,4]benzodiazepine a) 3-Fluoro-9H-imidazo[1,5-a][1,2,4]triazolo[1,5-d][1,4]benzodiazepine-10-carbaldehyd To a suspension of 3-fluoro-10-hydroxymethyl-9H-imidazo[1,5-a][1,2,4]triazolo[1,5-d][1,4]benzodiazepine (6.00 g, 22.1 mmol) in dichloromethane (200 mL) at 0° C. was added sodium bicarbonate (5.58 g, 66.4 mmol) and Dess-Martin periodinane (14.5 g, 33.2 mmol). After stirring at this temperature for 35 min it was allowed to warm to ambient temperature and stirred for another 1.5 h. Heptane (300 mL) and dichloromethane (100 mL) were added and the orange suspension was stirred for additional 2 h. After filtration through Hyflo® it was carefully washed with dichloromethane and evaporated. Purification of the residue by chromatography ($SiO_2$, ethyl acetate: methanol=19:1) afforded the title compound (5.12 g, 86%) as an off-white solid. MS: m/e=270.3 ($M+H^+$).

b) 3-Fluoro-10-difluoromethyl-9H-imidazo[1,5-a][1,2,4]triazolo[1,5-d][1,4]benzodiazepine To a suspension of 3-fluoro-9H-imidazo[1,5-a][1,2,4]triazolo[1,5-d][1,4]benzodiazepine-10-carbaldehyde (4.74 g, 17.6 mmol) in dichloromethane (200 mL) was added, at ambient temperature under argon, bis(2-methoxyethyl)aminosulphur trifluoride (16.6 mL, 90.0 mmol). The reaction mixture was stirred for 92 h. Again, bis(2-methoxyethyl)-aminosulphur trifluoride (3.8 mL) was added and stirring was continued for another 26 h at ambient temperature. The mixture was diluted with ethyl acetate and washed with aq $Na_2CO_3$, dried over sodium sulfate and concentrated in vacuo. The residue was purified by chromatography ($SiO_2$, heptane:ethyl acetate=1:1) affording the title compound (1.48 g, 29%) as a white solid. MS: m/e=292.1 (M+H$^+$).

EXAMPLE 5

3-Fluoro-10-trifluoromethyl-9H-imidazo[1,5-a][1,2,4]triazolo[1,5-d][1,4]benzodiazepine To a mixture of 3-fluoro-9H-imidazo[1,5-a][1,2,4]triazolo[1,5-d][1,4]benzodiazepine-10-carboxylic acid (500 mg, 1.75 mmol) and dichloromethane (35 mL) was added at −24° C. hydrogen fluoride (dest., 1.0 g) followed at −42° C. by sulfur tetrafluoride (dest., 1.0 g). The reaction mixture was heated to 80° C. for 3 h. The resulting yellow solution was concentrated and purified by chromatography ($SiO_2$, tert-butylmethylether) affording the title compound (90 mg, 17%) as a white solid. MS: m/e=310.1 (M+H$^+$).

EXAMPLE 6

3-Bromo-10-fluoromethyl-9H-imidazo[1,5-a][1,2,4]triazolo[1,5-d][1,4]benzodiazepine a) 4-Bromo-2-cyano-phenyl)-carbamic acid ethyl ester A suspension of 2-bromo-5-chlorobenzonitrile (58.5 g, 297 mmol) in ethyl chloroformate (141 mL, 1.48 mol) was heated at reflux for 5 h. The excess ethyl chloroformate (99 mL) was distilled off and toluene (96 mL) was added. Slow addition of cyclohexane (228 mL) induced crystallization. The resulting solid was collected by filtration and rinsed with cyclohexane. Drying in vacuo afforded the title compound (54.3 g, 68%) as an orange solid. MS: m/e=267.1/269.2 (M−H$^-$).

b) 9-Bromo-6H-[1,2,4]triazolo[1,5-c]quinazolin-5-one

To a solution of 4-bromo-2-cyano-phenyl)-carbamic acid ethyl ester (40.4 g, 150 mmol) in NMP (170 mL) was added formylhydrazine (10.0 g, 150 mmol). The resulting mixture was stirred for 1.5 h at 160° C. under a gentle nitrogen sweep. It was cooled to below 100° C. and water (340 mL) was added slowly. The resulting slurry was cooled to 25° C. and stirred for 15 min. The solid was collected by filtration and washed with water and 2-propanol. Drying in vacuo afforded the title compound (32.4 g, 81%) as a light yellow solid. MS: m/e=264.9/267.0 (M+H$^+$).

c) 4-Bromo-2-(2H-[1,2,4]triazol-3-yl)-phenylamine

To a well stirred slurry of 9-bromo-6H-[1,2,4]triazolo[1,5-c]quinazolin-5-one (32.0 g, 171 mmol) in ethylene glycol (146 mL) which was heated at 100° C., was added aq NaOH 32% (22.4 mL, 241 mmol). The slurry was heated at 140° C. for 17.5 h. The resulting solution was cooled to 27° C. and the product began to crystallize. Water (146 mL) and 1-octanol (1.73 mL) were added and the pH of the suspension was adjusted to 6.5 by the slow addition of glacial acetic acid (14 mL). The resulting slurry was stirred for 30 min, the solid was collected by filtration and washed with water and 2-propanol. Drying in vacuo afforded the title compound (25.2 g, 87%) as a light yellow solid. MS: m/e=239.0/241.1 (M+H$^+$).

d) 9-Bromo-6H-1,3,3a,6-tetraaza-benzo[e]azulen-5-one

A solution of 4-bromo-2-(2H-[1,2,4]triazol-3-yl)-phenylamine (25.0 g, 105 mmol) in dioxane (870 mL) and pyridine (10.0 mL) was cooled to 12° C. A solution of chloroacetyl chloride (9.56 mL, 121 mmol) in diethylether (34.7 mL) was added dropwise over a period of 8 min. The mixture was stirred at 10-12° C. for 75 min and treated within 5 min with aq NaOH 2N (126 mL, 251 mmol). The mixture was stirred for 17.5 h at ambient temperature. The pH thereby dropped to about pH=9 and it was adjusted to pH=8 with 3N HCl (6 mL). After evaporation the residue was stirred at 15° C. for 30 min in water (650 mL) and ethyl acetate (22 mL). The crystals were filtered off, washed with cold water and dried in vacuo. Trituration in ethyl acetate (100 mL) afforded the title compound (13.4 g, 46%) as a light yellow solid. MS: m/e=279.0/281.0 (M+H$^+$).

e) Ethyl 3-Bromo-9H-imidazo[1,5-a][1,2,4]triazolo[1,5-d][1,4]benzodiazepine-10-carboxylate To a suspension of 9-bromo-6H-1,3,3a,6-tetraaza-benzo[e]azulen-5-one (10.7 g, 38.5 mmol) in chloroform (270 mL, filtrated over Alox basic) was added N,N-dimethyl-p-toluidine (13.9 mL, 96.1 mmol) and phosphorous oxychloride (5.28 mL, 57.7 mmol). The mixture was stirred for 22 h at reflux, then cooled to 30° C. and poured into aq $NaHCO_3$ (10%, 575 mL). After extraction with chloroform (50 mL) the organic layers were dried over sodium sulfate and concentrated. In the meantime potassium tert-butylate (4.31 g, 38.5 mmol) was added in portions to a solution of ethyl isocyanoacetate (4.42 mL, 38.5 mmol) in THF (115 mL) at −25 to −10° C. The resulting suspension was stirred for 45 min at −10° C. and then cooled to −65° C. The solution from above was added dropwise within 10 min and the mixture was stirred for 16 h at ambient temperature. Acetic acid (1.6 mL) was added, stirred for 15 min and then poured into aq $NaHCO_3$ 5% (460 mL) and ethyl acetate (96 mL). The resulting crystals were filtered off, washed with ethyl acetate (25 mL), water (50 mL) and ethyl acetate (25 mL). Drying in vacuo afforded the title compound (4.81 g, 33%) as a light brown solid. MS: m/e=373.7/375.7 (M$^+$).

f) 3-Bromo-10-hydroxymethyl-9H-imidazo[1,5-a][1,2,4]triazolo[1,5-d][1,4]benzodiazepine As described for example 3a, ethyl 3-bromo-9H-imidazo[1,5-a][1,2,4]triazolo[1,5-d][1,4]benzodiazepine-10-carboxylate (1.03 g, 2.75 mmol), instead of ethyl 3-fluoro-9H-imidazo[1,5-a][1,2,4]triazolo[1,5-d][1,4]benzodiazepine-10-carboxylate, was converted to title compound (652 mg, 71%) which was obtained as a white solid. MS: m/e=332.1/334.1 (M+H$^+$).

g) 3-Bromo-10-fluoromethyl-9H-imidazo[1,5-a][1,2,4]triazolo[1,5-d][1,4]benzodiazepine As described for example 1b, 3-bromo-10-hydroxymethyl-9H-imidazo[1,5-a][1,2,4]triazolo[1,5-d][1,4]benzodiazepine (623 mg, 1.88 mmol), instead of 3-chloro-10-hydroxymethyl-9H-imidazo[1,5-a][1,2,4]triazolo[1,5-d][1,4]benzodiazepine, was converted to the title compound ($SiO_2$, heptane:ethyl acetate:dichloromethane=3:5:2, 249 mg, 40%) which was obtained as a white solid. MS: m/e=334.1/336.2 ($M+H^+$).

EXAMPLE 7

3-Bromo-10-difluoromethyl-9H-imidazo[1,5-a][1,2,4]triazolo[1,5-d][1,4]benzodiazepine a) 3-Bromo-9H-imidazo[1,5-a][1,2,4]triazolo[1,5-d][1,4]benzodiazepine-10-carbaldehyd As described for example 2a, 3-bromo-10-hydroxymethyl-9H-imidazo[1,5-a][1,2,4]triazolo[1,5-d][1,4]benzodiazepine (600 mg, 1.81 mmol), instead of 3-chloro-10-hydroxymethyl-9H-imidazo[1,5-a][1,2,4]triazolo[1,5-d][1,4]benzodiazepine, was converted to the title compound (208 mg, 35%) which was obtained as a white solid. MS: m/e=330.1/332.1 ($M+H^+$).

b) 3-Bromo-10-difluoromethyl-9H-imidazo[1,5-a][1,2,4]triazolo[1,5-d][1,4]benzodiazepine To a suspension of 3-bromo-9H-imidazo[1,5-a][1,2,4]triazolo[1,5-d][1,4]benzodiazepine-10-carbaldehyde (165 mg, 0.50 mmol) in dichloromethane (5 mL) was added [bis(2-methoxyethyl)amino]sulfur trifluoride (0.41 mL, 2.20 mmol) at ambient temperature. The mixture was stirred for 21 h and then separated between ethyl acetate and saturated aq $Na_2CO_3$. Drying over sodium sulfate and concentration was followed by purification by chromatography ($SiO_2$, ethyl acetate:dichloromethane:methanol=8:1:1) affording the title compound (99 mg, 56%) as an off-white solid. MS: m/e=351.7/353.6 ($M^+$).

EXAMPLE 8

3-Cyclopropyl-10-fluoromethyl-9H-imidazo[1,5-a][1,2,4]triazolo[1,5-d][1,4]benzodiazepine To a suspension of 3-bromo-10-fluoromethyl-9H-imidazo[1,5-a][1,2,4]triazolo[1,5-d][1,4]benzodiazepine (180 mg, 0.54 mmol) in THF (5 mL) was added under an argon atmosphere tetrakis(triphenylphosphine)palladium(0) (31 mg, 0.03 mmol) and cyclopropylzinc chloride (0.38 M in THF, 1.78 mL, 0.67 mmol). After stirring for 18 h at ambient temperature it was added again tetrakis(triphenylphosphine)palladium(0) (32 mg, 0.03 mmol) and cyclopropylzinc chloride (0.38 M in THF, 10 mL, 3.8 mmol) and the mixture was stirred for another 28 h. After addition of aq $NH_4Cl$ and extraction with ethyl acetate the combined organic layers were washed with aq $Na_2CO_3$, dried over sodium sulfate and concentrated. Purification of the residue by chromatography ($SiO_2$, heptane:ethyl acetate:dichloromethane=1:3:1) afforded the title compound (64 mg, 40%) as a light brown solid. MS: m/e=296.4 ($M+H^+$).

EXAMPLE 9

3-Cyclopropyl-10-difluoromethyl-9H-imidazo[1,5-a][1,2,4]triazolo[1,5-d][1,4]benzodiazepine As described for example 8, 3-bromo-10-difluoromethyl-9H-imidazo[1,5-a][1,2,4]triazolo[1,5-d][1,4]benzodiazepine (300 mg, 0.85 mmol), instead of 3-bromo-10-fluoromethyl-9H-imidazo[1,5-a][1,2,4]triazolo[1,5-d][1,4]benzodiazepine was converted to the title compound (61 mg, 23%) which was obtained as a white solid. MS: m/e=314.0 ($M+H^+$).

EXAMPLE 10

10-Difluoromethyl-3-ethyl-9H-imidazo[1,5-a][1,2,4]triazolo[1,5-d][1,4]benzodiazepine To a solution of 3-bromo-10-difluoromethyl-9H-imidazo[1,5-a][1,2,4]triazolo[1,5-d][1,4]benzodiazepine (211 mg, 0.60 mmol) in THF (4 mL) were added under an argon atmosphere bis(triphenylphosphine)palladium(II) chloride (21 mg, 0.03 mmol) and diethylzinc (1.0 M in hexane, 2.40 mL, 2.40 mmol). The resulting dark brown solution was stirred for 18 h at ambient temperature. After addition of aqueous $NH_4Cl$ (20 mL) and extraction with ethyl acetate the combined organic layers were dried over sodium sulfate and concentrated. Purification of the residue by chromatography ($SiO_2$, heptane:ethyl acetate:dichloromethane:methanol=75:15:10:0 to 0:80:10:10) afforded the title compound (107 mg, 59%) as an off-white solid. MS: m/e=302.2 ($M+H^+$).

EXAMPLE 11

3-Benzyl-10-difluoromethyl-9H-imidazo[1,5-a][1,2,4]triazolo[1,5-d][1,4]benzodiazepine To a solution of 3-bromo-10-difluoromethyl-9H-imidazo[1,5-a][1,2,4]triazolo[1,5-d][1,4]benzodiazepine (211 mg, 0.60 mmol) in THF (4 mL) were added under an argon atmosphere bis(triphenylphosphine)palladium(II) chloride (21 mg, 0.03 mmol) and benzylzinc bromide (0.5 M in THF, 4.80 mL, 2.40 mmol). The resulting dark brown solution was stirred for 17 h at 50° C. After addition of aqueous $NH_4Cl$ (20 mL) and extraction with ethyl acetate the combined organic layers were dried over sodium sulfate and concentrated. Purification of the residue by chromatography ($SiO_2$, heptane:ethyl acetate:dichloromethane:methanol=75:15:10:0 to 0:80:10:10) afforded the title compound (179 mg, 82%) as a light yellow foam. MS: m/e=364.3 ($M+H^+$).

EXAMPLE 12

10-Difluoromethyl-3-ethynyl-9H-imidazo[1,5-a][1,2,4]triazolo[1,5-d][1,4]benzodiazepine a) 10-Difluoromethyl-3-trimethylsilyanylethynyl-9H-imidazo[1,5-a][1,2,4]triazolo[1,5-d][1,4]benzodiazepine A suspension of 3-bromo-10-difluoromethyl-9H-imidazo[1,5-a][1,2,4]triazolo[1,5-d][1,4]benzodiazepine (352 mg, 1.00 mmol), trimethylsilylacetylene (221 μl, 1.55 mmol), bis(triphenylphosphine)-palladium(II) chloride (35 mg, 0.05 mmol), triphenylphosphine (8 mg, 0.03 mmol) and triethylamine (0.50 mL, 3.6 mmol) in THF (5 mL) was stirred for 15 min at ambient temperature. Copper(I) bromide (1.4 mg, 0.01 mmol) was added and the reaction mixture was stirred for 17 h at 70° C. under an argon atmosphere. The mixture was diluted with ethyl acetate (20 mL) and washed with aqueous citric acid (10%, 40 mL). The aqueous phase was extracted with ethyl acetate (40 mL) and the combined organic layers were dried over sodium sulfate. Purification by chromatography (SiO$_2$, heptane:ethyl acetate:dichloromethane:methanol=75:15:10:0 to 0:80:10:10) afforded the title compound (344 mg, 93%) as a light yellow foam. MS: m/e=370.1 [M+H]$^+$.

b) 10-Difluoromethyl-3-ethynyl-9H-imidazo[1,5-a][1,2,4]triazolo[1,5-d][1,4]benzodiazepine To a solution of 10-difluoromethyl-3-trimethylsilanylethynyl-9H-imidazo[1,5-a][1,2,4]triazolo[1,5-d]-[1,4]benzodiazepine (259 mg, 0.70 mmol) in a mixture of THF (2.5 mL) and MeOH (0.25 mL) was added under an argon atmosphere at −70° C. tetrabutylammonium fluoride trihydrate (232 mg, 0.74 mmol). After stirring for 30 min at this temperature, the dry ice bath was replaced with an ice bath and the reaction mixture was stirred for 1 h at 0° C. It was diluted with ethyl acetate (10 mL), washed with aqueous Na$_2$CO$_3$ and extracted with ethyl acetate (10 mL). Drying over sodium sulfate and purification by chromatography (SiO2, heptane:ethyl acetate:dichloromethane:methanol=75:15:10:0 to 0:80:10:10) afforded the title compound (201 mg, 97%) as a white solid. MS: m/e=298.2 [M+H]$^+$.

EXAMPLE 13

3-Cyano-10-difluoromethyl-9H-imidazo[1,5-a][1,2,4]triazolo[1,5-d][1,4]benzodiazepine A mixture of 3-bromo-10-difluoromethyl-9H-imidazo[1,5-a][1,2,4]triazolo[1,5-d][1,4]benzodiazepine (211 mg, 0.60 mmol), tetrakis(triphenylphosphine)palladium(0) (21 mg, 0.02 mmol) and zinc cyanide (70 mg, 0.60 mmol) in DMF (4 mL) was stirred under an argon atmosphere for 42 h at reflux. Further tetrakis(triphenyl-phosphine)palladium(0) (21 mg, 0.02 mmol) and zinc cyanide (70 mg, 0.60 mmol) were added and stirring was continued for another 24 h at reflux. The reaction mixture was poured into a solution of iron(III) chloride (973 mg, 6.0 mmol) in aqueous HCl (1N, 5.0 mL) and ethyl acetate (30 mL) at 0° C. After stirring for 1 h at this temperature the mixture was basified with aqueous Na$_2$CO$_3$ (2N), filtered over Hyflo® and washed with ethyl acetate. After extraction of the aqueous layer with ethyl acetate the combined organic layers were washed with water and brine, dried over sodium sulfate and concentrated. Purification of the residue by chromatography (SiO$_2$, heptane:ethyl acetate:dichloromethane:methanol=75:15:10:0 to 0:80:10:10:) afforded the title compound (74 mg, 42%) as a white solid. MS: m/e=299.2 (M+H$^+$).

EXAMPLE 14

10-(1,1-Difluoro-ethyl)-3-fluoro-9H-imidazo[1,5-a][1,2,4]triazolo[1,5-d][1,4]benzodiazepine a) 1-[3-Fluoro-9H-imidazo[1,5-a][1,2,4]triazolo[1,5-d][1,4]benzodiazepin-10-yl]-ethanone To a solution of 10-cyano-3-fluoro-9H-imidazo[1,5-a][1,2,4]triazolo[1,5-d][1,4]benzodiazepine$^1$ (2.07 g, 7.78 mmol) in THF (100 mL) was added at ambient temperature methylmagnesium bromide (3N in Et$_2$O, 39.0 mL, 13.0 mmol) over a period of 5 min. The resulting clear brown solution was stirred for another 2 h. The mixture was carefully poured into aq. HCl (1N, 200 mL) and extracted with ethyl acetate (3× 200 mL). The combined organic layers were washed with water (250 mL) and brine (250 mL), dried over sodium sulfate and concentrated. Purification of the residue by chromatography (SiO$_2$, heptane:ethyl acetate:methanol=20:80:0 to 0:90:10) afforded the title compound (303 mg, 14%) as a white solid. MS: m/e=282.4 (M−H$^-$).

b) 10-(1,1-Difluoro-ethyl)-3-fluoro-9H-imidazo[1,5-a][1,2,4]triazolo[1,5-d][1,4]benzodiazepine A mixture of 1-[3-fluoro-9H-imidazo[1,5-a][1,2,4]triazolo[1,5-d][1,4]benzodiazepin-10-yl]-ethanone (100 mg, 0.35 mmol) and bis(2-methoxyethyl)aminosulphur trifluoride (50% in THF, 1.56 mL, 3.53 mmol) was stirred for 3 days at 60° C. in a closed plastic tube under an argon atmosphere. The mixture was diluted with ethyl acetate (20 mL) and washed with aqueous Na$_2$CO$_3$ (sat.). Extracted with ethyl acetate (20 mL) was followed by drying over sodium sulfate and concentration. Purification of the residue by chromatography (SiO$_2$, heptane:ethyl acetate:dichloromethane=60:20:20 to 30:50:20:) afforded the title compound (24 mg, 22%) as a light brown solid. MS: m/e=306.2 (M+H$^+$).

EXAMPLE 15

10-(1,1-Difluoro-propyl)-3-fluoro-9H-imidazo[1,5-a][1,2,4]triazolo[1,5-d][1,4]benzodiazepine a) 3-Fluoro-9H-imidazo[1,5-a][1,2,4]triazolo[1,5-d][1,4]benzodiazepine-10-carboxylic acid methoxy-methyl-amide A mixture of 3-fluoro-9H-imidazo[1,5-a][1,2,4]triazolo[1,5-d][1,4]benzodiazepine-10-carboxylic acid (20.74 g, 72.7 mmol), N,O-dimethylhydroxylamine hydrochloride (11.35 g, 116.3 mmol), 1-(3-dimethylaminopropyl)-3-ethylcarbodiimide hydrochloride (16.72 g, 87.24 mmol), N-methylmorpholine (12.78 mL, 116.3 mmol) and N,N-dimethylaminopyridine (300 mg, 3.23 mmol) in a mixture of THF (200 mL) and DMF (40 mL) was stirred at ambient temperature for 18 h. The dichloromethane was distilled off and ice cold water (200 mL) was added. The resulting suspension was stirred for 15 min, filtered and washed with water (100 mL). Drying afforded the title compound (11.46 g, 48%) as white solid. MS: m/e=329.1 (M+H$^+$).

b) 1-[3-Fluoro-9H-imidazo[1,5-a][1,2,4]triazolo[1,5-d][1,4]benzodiazepin-10-yl]-propan-1-one To a solution of 3-fluoro-9H-imidazo[1,5-a][1,2,4]triazolo[1,5-d][1,4]benzodiazepine-10-carboxylic acid methoxy-methyl-amide (500 mg, 1.52 mmol) in THF (20 mL) was added at −70° C. ethyl magnesium bromide (3M in THF, 1.52 mL, 4.57 mmol). The dry ice bath was removed and the reaction mixture was stirred for 2 h. After cooling to −70° C. further ethyl magnesium bromide (3M in THF, 1.52 mL, 4.57 mmol) was added and the mixture stirred for another 2 h at ambient temperature. The mixture was cooled to 0° C. and aqueous HCl (1N, 10 mL) was added dropwise. It was diluted with ethyl acetate (20 mL) and aqueous Na$_2$CO$_3$ (sat.). The aqueous layer was extracted with ethyl acetate and the combined organic layers were washed with aqueous Na$_2$CO$_3$ (sat.). Drying over sodium sulfate and purification of the residue by chromatography (SiO$_2$, heptane:ethyl acetate: dichloromethane=60:20:20 to 30:50:20:) afforded the title compound (200 mg, 44%) as a white solid. MS: m/e=298.2 (M+H$^+$).

c) 10-(1,1-Difluoro-propyl)-3-fluoro-9H-imidazo[1,5-a][1,2,4] triazolo[1,5-d][1,4]benzodiazepine A mixture of 1-[3-fluoro-9H-imidazo[1,5-a][1,2,4]triazolo[1,5-d][1,4]benzodiazepin-10-yl]-propan-1-one (158 mg, 0.53 mmol), bis(2-methoxyethyl)aminosulphur trifluoride (490 µL, 2.66 mmol) and ethanol (10 µL, 0.16 mmol) was stirred for 2 d at 90° C. in a closed plastic tube under an argon atmosphere. The reaction mixture was poured onto ice/water and was extracted with ethyl acetate (20 mL). The organic layers were washed with aqueous Na$_2$CO$_3$ and dried over sodium sulfate. Purification of the residue by chromatography (SiO$_2$, heptane:ethyl acetate:dichloromethane=60: 20:20 to 30:50:20:) afforded the title compound (41 mg, 24%) as an off-white solid. MS: m/e=320.0 (M+H$^+$).

EXAMPLE 16

10-Difluoromethyl-9H-imidazo[1,5-a][1,2,4]triazolo [1,5-d][1,4]benzodiazepine

To a solution of 3-bromo-10-difluoromethyl-9H-imidazo [1,5-a][1,2,4]triazolo[1,5-d][1,4]benzodiazepine (247 mg, 0.70 mmol) in methanol (10 mL) was added under an argon atmosphere palladium/charcoal (10%, 74 mg, 0.07 mmol). The mixture was then stirred for 17 h at ambient temperature under a hydrogene atmosphere before filtered over Hyflo® and washed with methanol. Purification of the residue by chromatography (SiO$_2$, heptane:ethyl acetate:dichloromethane:methanol=75:15:10:0 to 0:80:10:10 ) afforded the title compound (122 mg, 64%) as a white solid. MS: m/e=274.2 (M+H$^+$).

EXAMPLE 17

3-Morpholin-4-yl-10-difluoromethyl-9H-imidazo[1,5-a][1,2,4]triazolo[1,5-d][1,4]benzodiazepine A mixture of 3-fluoro-10-difluoromethyl-9H-imidazo[1,5-a][1,2,4]triazolo[1,5-d][1,4]benzodiazepine (200 mg, 0.69 mmol) and morpholine (0.30 mL, 03.43 mmol) in DMSO (2 mL) was stirred in a closed reaction tube for 18 h at 130° C. The reaction mixture was diluted with ethyl acetate (20 mL), washed twice with aqueous sodium carbonate (saturated), dried over sodium sulfate and concentrated. Purification of the residue by chromatography (SiO$_2$, heptane:ethyl acetate: dichloromethane:methanol=60:20:20:0 to 20:50:20:10:) afforded the title compound (138 mg, 56%) as a white solid. MS: m/e=359.2 (M+H$^+$).

EXAMPLE 18

3-Bromo-10-(1-fluoro-propyl)-9H-imidazo[1,5-a][1,2,4]triazolo[1,5-d][1,4]benzodiazepine a) 3-Bromo-10-(1-hydroxy-propyl)-9H-imidazo[1,5-a][1,2,4]triazolo[1,5-d][1,4]benzodiazepine To a suspension of 3-bromo-9H-imidazo[1,5-a][1,2,4]triazolo[1,5-d][1,4]benzodiazepine-10-carbaldehyde (500 mg, 1.51 mmol) in THF (25 mL) was added ethylmagnesium bromide solution (3 M in THF, 3.03 mL, 9.09 mmol) at −70° C. After 1 h at this temperature aqueous ammonium chloride (saturated, 18 mL) was added and the mixture was warmed to ambient temperature. After addition of dichloromethane and aqueous sodium carbonate it was extracted (dichloromethane) and the combined organic layers were washed with water and dried over sodium sulfate. Purification of the residue by chromatography (SiO$_2$, heptane:ethyl acetate: methanol=80:19:01 to 0:90:10) afforded the tide compound (413 mg, 76%) as a white solid. MS: m/e=360.0/362.0 (M+H$^+$).

b) 3-Bromo-10-(1-fluoro-propyl)-9H-imidazo[1,5-a] [1,2,4]triazolo[1,5-d][1,4]benzodiazepine To a solution of 3-bromo-10-(1-hydroxy-propyl)-9H-imidazo[1,5-a][1,2,4]triazolo[1,5-d][1,4]benzodiazepine (260 mg, 0.72 mmol) in dichloromethane (7 mL) was added at −70° C. bis(2-methoxyethyl)aminosulphur trifluoride (110 µL, 1.08 mmol). The resulting mixture was stirred for 19 h while allowing to warm to ambient temperature. After addition of dichloromethane (20 mL) it was washed with aqueous sodium carbonate (saturated) and dried over sodium sulfate. Purification of the residue by chromatography (SiO$_2$, heptane:ethyl acetate:dichloromethane=70:20:10 to 00:90:10:) afforded the tide compound (60 mg, 23%) as an off-white solid. MS: m/e=362.0/364.0 (M+H$^+$).

EXAMPLE 19

3-Bromo-10-(1,1-difluoro-propyl)-9H-imidazo[1,5-a][1,2,4]triazolo[1,5-d][1,4]benzodiazepine a) 3-Bromo-10-(2-ethyl-[1,3]dithian-2-yl)-9H-imidazo[1,5-a][1,2,4]triazolo[1,5-d][1,4]benzodiazepine To a suspension of 1-[3-bromo-9H-imidazo[1,5-a][1,2,4] triazolo[1,5-d][1,4]benzodiazepin-10-yl]-propan-1-one (410 mg, 1.14 mmol) in dioxane (7.5ml) was added 1,2-ethanedithiol (578 µl, 6.87 mmol) and boron trifluoride acetic acid complex (636 µl, 4.58 mmol). The given solution was stirred for 4 d at 60° C. under an argon atmosphere, then cooled to ambient temperature and quenched with aqueous sodium hydrogencarbonate (saturated, 30 ml). After stirring for 30 min at ambient temperature, the mixture was extracted with ethyl acetate. Washing with aqueous sodium hydrogencarbonate (saturated), aqueous sodium hydroxide (15%) and brine was followed by drying over sodium sulfate. Purification of the residue by chromatography (SiO$_2$, heptane:ethyl acetate:dichloromethane:methanol=75:15:10:0 to 0:70:10:20:) afforded the title compound (364 mg, 73%) as a white solid. MS: m/e=434.0/436.0 (M+H$^+$).

b) 3-Bromo-10-(1,1-difluoro-propyl)-9H-imidazo[1,5-a][1,2,4]triazolo[1,5-d][1,4]benzodiazepine To a suspension of N-iodosuccinimide (678 mg, 3.01 mmol) in dichloromethane (6.6ml) was added HF-pyridine (390 µl, 1.66 mmol) at −30° C. Then a solution of 3-bromo-10-(2-ethyl-[1,3]dithian-2-yl)-9H-imidazo[1,5-a][1,2,4]triazolo[1,5-d][1,4]benzodiazepine (327 mg, 0.75 mmol) in dichloromethane (1.7 ml) was added dropwise at −30° C. The resulting dark red mixture was stirred for another 15 min at −30° C., then poured cautiously onto ice-cold aqueous sodium hydrogencarbonate (saturated, 50 ml) and stirred for 5 min. The mixture was extracted with dichloromethane. The organic layers were washed with aqueous sodium hydrogencarbonate (saturated), brine and were dried over sodium sulfate. Purification of the residue by chromatography (SiO$_2$, heptane:ethyl acetate:dichloromethane:methanol=75:15:10:0 to 0:70:10:20:) afforded the title compound (231 mg, 81%) as a white solid. MS: m/e=380.0/382.0 (M+H$^+$).

EXAMPLE 20

3-Chloro-10-fluoromethyl-6-methyl-9H-imidazo[1,5-a][1,2,4]triazolo[1,5-d][1,4]benzodiazepine To a mixture of ethyl 3-chloro-6-methyl-9H-imidazo[1,5-a][1,2,4]triazolo[1,5-d][1,4]benzodiazepine-10-carboxylate (300 mg, 0.87 mmol) in THF (mL) was added lithium borohydride (23 mg, 1.05 mmol) at ambient temperature. The resulting suspension was stirred at reflux for 5 h. After the reaction mixture was cooled to ambient temperature aqueous ammonium chloride (saturated, 5 mL) was added carefully and the resulting mixture was stirred at this temperature for 18 h. The organic solvent was distilled off and the resulting suspension filtered and washed with water. The residue was dissolved in dichloromethane (8 mL) and bis(2-methoxyethyl)aminosulphur trifluoride (161 μL, 0.87 mmol) was added and the reaction mixture was stirred for 18 h at ambient temperature. It was diluted with dichloromethane (20 mL) and washed with aqueous sodium carbonate (saturated). Drying over sodium sulfate and purification of the residue by chromatography (SiO$_2$, heptane:ethyl acetate:dichloromethane:methanol=40:40:20:0 to 0:75:20:5:) afforded the title compound (67 mg, 28%) as a white solid. MS: m/e=304.1 (M+H$^+$).

EXAMPLE 21

3-Chloro-6-(3,4-dimethoxyphenyl)-10-fluoromethyl-9H-imidazo[1,5-a][1,2,4]triazolo[1,5-d][1,4]benzodiazepine Ethyl 3-Chloro-6-(3,4-dimethoxyphenyl)-9H-imidazo[1,5-a][1,2,4]triazolo[1,5-d][1,4]benzodiazepine-10-carboxylate (300 mg, 0.64 mmol), instead of ethyl 3-chloro-6-methyl-9H-imidazo[1,5-a][1,2,4]triazolo[1,5-d][1,4]benzodiazepine-10-carboxylate as described in example 20 was converted to the title compound (112 mg, 41%) which was obtained as a white solid. MS: m/e=425.9 (M+H$^+$).

The invention claimed is:
1. A compound of formula I

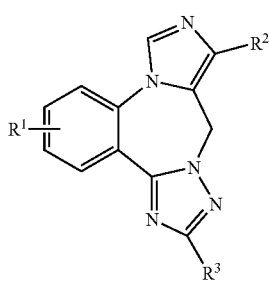

wherein
R$^1$ is hydrogen, halogen, lower alkyl lower alkynyl, cycloalkyl, heterocycloalkyl, benzyl, cyano, lower alkoxy, OCF$_3$, —NHR, —NHC(O)R or —NHSO$_2$R;
R$^2$ is lower alkyl substituted by halogen;

R$^3$ is hydrogen, methyl or aryl;
R is lower alkyl, cycloalkyl or aryl;
or a pharmaceutically acceptable acid addition salt thereof.
2. A compound of claim 1 having formula I-A

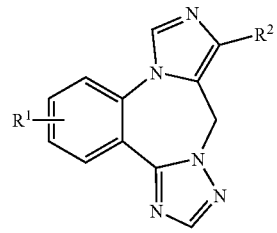

wherein
R$^1$ is hydrogen, halogen, lower alkyl, lower alkynyl, cycloalkyl, benzyl, cyano, lower alkoxy, OCF$_3$, —NHR, —NHC(O)R or —NHSO$_2$R;
R$^2$ is lower alkyl substituted by halogen;
R is lower alkyl, cycloalkyl or aryl;
and their pharmaceutically acceptable acid addition salts.
3. A compound of claim 1 in which R$^2$ is CH$_2$F.
4. A compound of claim 3, selected from the group consisting of
3-chloro-10-fluoromethyl-9H-imidazo[1,5-a][1,2,4]triazolo[1,5-d][1,4]benzodiazepine,
3-fluoro-10-fluoromethyl-9H-imidazo[1,5-a][1,2,4]triazolo[1,5-d][1,4]benzodiazepine,
3-bromo-10-fluoromethyl-9H-imidazo[1,5-a][1,2,4]triazolo[1,5-d][1,4]benzodiazepine,
3-cyclopropyl-10-fluoromethyl-9H-imidazo[1,5-a][1,2,4]triazolo[1,5-d][1,4]benzodiazepine and
3-chloro-10-fluoromethyl-6-methyl-9H-imidazo[1,5-a][1,2,4]triazolo[1,5-d][1,4]benzodiazepine.
5. A compound of claim 1 in which R$^2$ is CHF$_2$.
6. A compound of claim 5, selected from the group consisting of
3-chloro-10-difluoromethyl-9H-imidazo[1,5-a][1,2,4]triazolo[1,5-d][1,4]benzodiazepine,
3-fluoro-10-difluoromethyl-9H-imidazo[1,5-a][1,2,4]triazolo[1,5-d][1,4]benzodiazepine,
3-bromo-10-difluoromethyl-9H-imidazo[1,5-a][1,2,4]triazolo[1,5-d][1,4]benzodiazepine,
3-cyclopropyl-10-difluoromethyl-9H-imidazo[1,5-a][1,2,4]triazolo[1,5-d][1,4]benzodiazepine,
10-difluoromethyl-3-ethyl-9H-imidazo[1,5-a][1,2,4]triazolo[1,5-d][1,4]benzodiazepine,
3-benzyl-10-difluoromethyl-9H-imidazo[1,5-a][1,2,4]triazolo[1,5-d][1,4]benzodiazepine,
10-difluoromethyl-3-ethynyl-9H-imidazo[1,5-a][1,2,4]triazolo[1,5-d][1,4]benzodiazepine,
3-cyano-10-difluoromethyl-9H-imidazo[1,5-a][1,2,4]triazolo[1,5-d][1,4]benzodiazepine and
10-difluoromethyl-9H-imidazo[1,5-a][1,2,4]triazolo[1,5-d][1,4]benzodiazepine.
7. A compound of claim 1 in which R$^2$ is CF$_3$.
8. A compound of claim 7, which is
3-fluoro-10-trifluoromethyl-9H-imidazo[1,5-a][1,2,4]triazolo[1,5-d][1,4]benzodiazepine.

9. A compound of claim 1 in which $R^2$ is $CF_2CH_3$ or $CF_2CH_2CH_3$.

10. A compound of claim 9, selected from the group consisting of
- 10-(1,1-difluoro-ethyl)-3-fluoro-9H-imidazo[1,5-a][1,2,4]triazolo[1,5-d][1,4]benzodiazepine,
- 10-(1,1-difluoro-propyl)-3-fluoro-9H-imidazo[1,5-a][1,2,4]triazolo[1,5-d][1,4]benzodiazepine, and
- 3-bromo-10-(1,1-difluoro-propyl)-9H-imidazo[1,5-a][1,2,4]triazolo[1,5-d][1,4]benzodiazepine.

11. A compound of claim 1, which is
3-chloro-6-(3,4-dimethoxyphenyl)-10-fluoromethyl-9H-imidazo[1,5-a][1,2,4]triazolo[1,5-d][1,4]benzodiazepine.

12. A pharmaceutical composition comprising a therapeutically effective amount of a compound of formula I

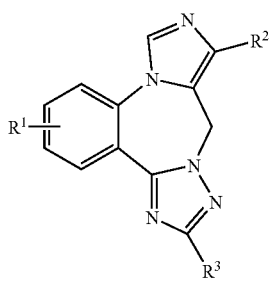

wherein
$R^1$ is hydrogen, halogen, lower alkyl, lower alkynyl, cycloalkyl, heterocycloalkyl, benzyl, cyano, lower alkoxy, $OCF_3$, —NHR, —NHC(O)R or —$NHSO_2R$;
$R^2$ is lower alkyl substituted by halogen;
$R^3$ is hydrogen, methyl or aryl;
R is lower alkyl, cycloalkyl or aryl;
or a pharmaceutically acceptable acid addition salt thereof and a pharmaceutically acceptable carrier.

13. A process for preparation of a compound of formula I

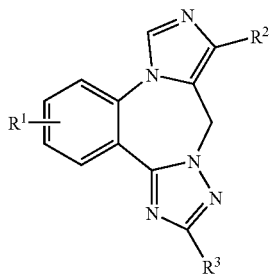

wherein
$R^1$ is hydrogen, halogen, lower alkyl, lower alkynyl, cycloalkyl, heterocycloalkyl, benzyl, cyano, lower alkoxy, $OCF_3$, —NHR, —NHC(O)R or —$NHSO_2R$;
$R^2$ is lower alkyl substituted by halogen;
$R^3$ is hydrogen, methyl or aryl;
R is lower alkyl, cycloalkyl or aryl;
or a pharmaceutically acceptable acid addition salt thereof wherein the process is selected from the group consisting of
a) reacting a compound of formula

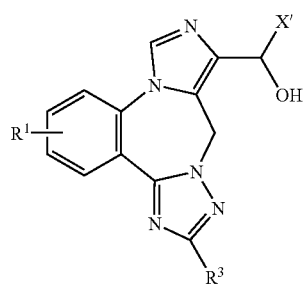

X' = H, lower alkyl with a suitable halogen-transfer-reagent to produce a compound of formula

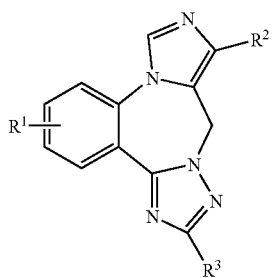

wherein $R^2$ is lower alkyl substituted by halogen;
b) reacting a compound of formula

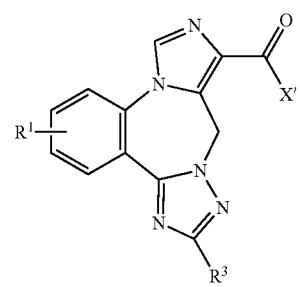

X' = H, lower alkyl with a suitable halogen-transfer-reagent to produce a compound of formula

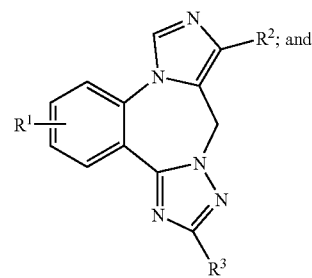

c) reacting a compound of formula

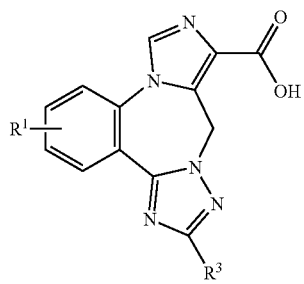

V with sulfur tetrafluoride in the presence of a hydrogen halogenide to produce a compound of formula

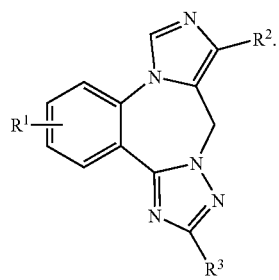

I

14. A method for enhancing cognition or treating a disorder selected from the group consisting of cognitive disorders, schizophrenia, anxiety and Alzheimer's disease comprising administering to an individual a therapeutically effective amount of a compound of formula I

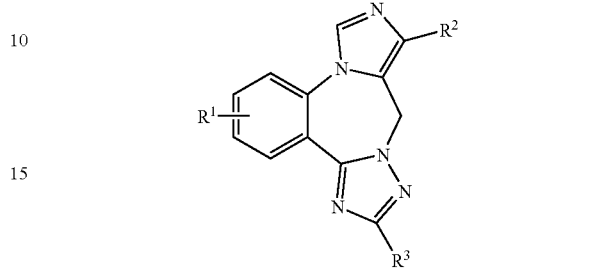

I wherein
$R^1$ is hydrogen, halogen, lower alkyl, lower alkynyl, cycloalkyl, heterocycloalkyl, benzyl, cyano, lower alkoxy, $OCF_3$, —NHR, —NHC(O)R or —NHSO$_2$R;
$R^2$ is lower alkyl substituted by halogen;
$R^3$ is hydrogen, methyl or aryl;
R is lower alkyl, cycloalkyl or aryl;
or a pharmaceutically acceptable acid addition salt thereof.

15. The method of claim 14, wherein the disorder is Alzheimer's disease.

* * * * *